(12) United States Patent
  Allred et al.

(10) Patent No.:  US 12,692,526 B2
(45) Date of Patent:       Jul. 28, 2026

(54) ENZYMATIC SYNTHESIS OF OLIGONUCLEOTIDES

(71) Applicant: MGI Holdings Co., Limited, Shenzhen (CN)

(72) Inventors: Benjamin Allred, San Jose, CA (US); Handong Li, San Jose, CA (US)

(73) Assignee: MGI Holdings Co., Limited, Shenzhen (CN)

( * ) Notice:  Subject to any disclaimer, the term of this patent is extended or adjusted under 35 U.S.C. 154(b) by 1059 days.

(21) Appl. No.: 17/769,998

(22) PCT Filed: Nov. 30, 2020

(86) PCT No.: PCT/CN2020/132637
  § 371 (c)(1),
  (2) Date: Apr. 18, 2022

(87) PCT Pub. No.: WO2021/104514
  PCT Pub. Date: Jun. 3, 2021

(65) Prior Publication Data
  US 2024/0271171 A1      Aug. 15, 2024

Related U.S. Application Data

(60) Provisional application No. 62/941,973, filed on Nov. 29, 2019.

(51) Int. Cl.
  *C12P 19/34*      (2006.01)
  *C12N 9/12*      (2006.01)
  *C12Q 1/6853*      (2018.01)

(52) U.S. Cl.
  CPC ............ *C12P 19/34* (2013.01); *C12N 9/1241* (2013.01); *C12Q 1/6853* (2013.01)

(58) Field of Classification Search
  CPC ..... C12P 19/34; C12N 9/1241; C12Q 1/6853; C12Q 2525/186; C12Q 2537/157
  See application file for complete search history.

(56) References Cited

U.S. PATENT DOCUMENTS

| | | | |
|---|---|---|---|
| 7,915,201 | B2 | 3/2011 | Franch et al. |
| 9,295,965 | B2 | 3/2016 | Jacobson et al. |

FOREIGN PATENT DOCUMENTS

| | | |
|---|---|---|
| CN | 107074903 A | 8/2017 |
| CN | 109312493 A | 2/2019 |
| CN | 109715824 A | 5/2019 |
| CN | 110158157 A | 8/2019 |
| WO | 2017007925 A1 | 1/2017 |
| WO | 2019070593 A1 | 4/2019 |
| WO | 2019121500 A1 | 6/2019 |

OTHER PUBLICATIONS

Opel KL et al. A Study of PCR Inhibition Mechanisms Using Real Time PCR. Journal of Forensic Sciences. 2010. vol. 55, No. 1. p. 25-33 (Year: 2010).*
Palluk et al., De Novo DNA Synthesis Using Polymerase-Nucleotide Conjugates, Nature Biotechnology, vol. 36, Issue 7, Jun. 18, 2018, 9 pages.
International Application No. PCT/CN2020/132637, International Preliminary Report on Patentability mailed on Jun. 9, 2022, 6 pages.
International Application No. PCT/CN2020/132637, International Search Report and the Written Opinion mailed on Feb. 25, 2021, 11 pages.
International Application No. PCT/CN2020/132637, Supplementary International Search Report and Written Opinion mailed on Jun. 7, 2021, 10 pages.
European Application No. 20893785.4, Extended European Search Report mailed On Dec. 18, 2023, 9 pages.
Hoff et al., Rapid and Dynamic Nucleic Acid Hybridization Enables Enzymatic Oligonucleotide Synthesis by Cyclic Reversible Termination, Available Online at: https://www.biorxiv.org/content/10.1101/561092v1.full.pdf+html, Feb. 27, 2019, 24 pages.

* cited by examiner

*Primary Examiner* — Paul J Holland
(74) *Attorney, Agent, or Firm* — Kilpatrick Townsend & Stockton LLP

(57) ABSTRACT

Provided are compositions and methods directed to using a short template and a polymerase or ligase to synthesize an oligonucleotide. The template is designed such that only one nucleotide is added to the primer in each round of synthesis.

19 Claims, 6 Drawing Sheets

Specification includes a Sequence Listing.

| Cycle | Step 1 | Step 2 |
|---|---|---|
| 1 | ATP-b — Surface-Attached Primer —3' + Template 1 (5'—3')  Extend 1 → | Deblock → (3' A-b) |
| 2 | CTP-b — A + Template 2 (5'—3')  Extend 2 → | Deblock → (3' AC-b) |
| n | AC — Repeat Extend, Deblock ⟹ | ACNNN... |

Minimal Template

Cycle    5        6        7        8        9        10

Base     C        T        C        T        C        T

Sucessfully elongated 10 cycles

| Cycle | DNA | Elongation | Deblock |
|---|---|---|---|
| 1 | ▯—TCTCT-3' | GAGAGA CTP-N$_3$ Polymerase | TPP |
| 2 | ▯—TCTCT C | AGAGAG TTP-N$_3$ Polymerase | TPP |
| 3 | ▯—TCTCT C T | GAGAGA CTP-N$_3$ Polymerase | TPP |
| 4 | ▯—TCTCT C T C | AGAGAG TTP-N$_3$ Polymerase | TPP |
| ... | | | |
| | ▯— 1 2 3 4 5 6 7 8 9 10 <br> C T C T C T C T C  T  (SEQ ID NO.:4) | | |

←— Unlabeled 10 mer
←— Unreactive primer $$stepwise\ yield = \left( \frac{product\ band}{lane\ total - unreactive\ primer} \right)^{\frac{1}{10}}$$

ENZYMATIC SYNTHESIS OF OLIGONUCLEOTIDES

CROSS-REFERENCES TO RELATED APPLICATIONS

This application is a national phase application of PCT Application No. PCT/CN2020/132637, filed Nov. 30, 2020, which claims the benefit of and priority to U.S. Provisional Application No. 62/941,973 filed on Nov. 29, 2019, which are hereby incorporated by reference in their entirety.

REFERENCE TO AN ELECTRONIC SEQUENCE LISTING

The contents of the electronic sequence listing (name 107445-1306608-5086-US SL.txt; Size: 866 bytes; and Date of Creation: Jul. 28, 2025) is herein incorporated by reference in its entirety.

BACKGROUND OF THE INVENTION

Synthetic DNA is currently produced with organic solvents and reagents, which has several undesirable consequences. First, side-reactions and incomplete reactions limit the yield of each synthetic step, which decreases the purity and length of oligonucleotide that can be produced. Second, the addition of each base requires a minimum of three different steps, but most high-purity processes use 6-8 steps, each of which takes time and increases instrument complexity. Lastly, the process generates a large amount of hazardous and expensive waste.

The drawbacks of chemical synthesis have motivated many efforts over several years to develop enzymatic synthesis methods and reagents. See, e.g., Hoff et al., 2019, "Rapid and dynamic nucleic acid hybridization enables enzymatic oligonucleotide synthesis by cyclic reversible termination" BioRxiv dx.doi.org/10.1101/561092; Kranz et al., 2018, "Enzymatic synthesis of nucleic acid sequences," US 2018/0195099. The potential advantages of enzymatic synthesis include higher yields and longer oligonucleotide products, faster production, a two-step process, and non-hazardous aqueous waste. However, in practice, enzymatic synthesis is not yet comparable to chemical synthesis in yield and flexibility.

SUMMARY OF THE INVENTION

In one aspect, the disclosure features a method for synthesizing a plurality of oligonucleotides, comprising: (a) providing a plurality of immobilized primers, wherein the 5' terminus of each primer is attached to a solid support; (b) combining the plurality of immobilized primers and (i) a plurality of templates comprising between 2 and 100 nucleotides, wherein each template hybridizes to a primer with one, two, three, or more than three overhang nucleotides at the 5' terminus of the template; (ii) a plurality of unincorporated nucleotides; and (iii) a polymerase; wherein the plurality of the immobilized primers are extended at the 3' terminus by the polymerase-mediated incorporation of one unincorporated nucleotide, wherein the incorporated nucleotide is complementary to the overhang nucleotide of the template hybridized to the primer; and then (c) removing the hybridized templates and excess unincorporated nucleotides; and (d) repeating steps (b) and (c) one or more times until the synthesis of the oligonucleotide is complete. In some embodiments, the templates hybridize to a primer with one overhang nucleotide. In some embodiments, the templates hybridize to a primer with three overhang nucleotides.

In some embodiments, the templates in the plurality of templates comprise between 5 and 50 nucleotides. In some embodiments, the templates in the plurality of templates comprise between 5 and 20 nucleotides. In some embodiments, the templates in the plurality of templates comprise between 4 and 25 nucleotides, or between 5 and 18 nucleotides, or between 5 and 15 nucleotides.

In some embodiments the unincorporated nucleotides are deoxyribonucleotides (dNTPs). In some embodiments the unincorporated nucleotides are ribonucleotides (NTPs). In this disclosure, unless otherwise clear from context, all references to "nucleotides" or to "NTP" or equivalents is specifically intended to encompass deoxyribonucleotides (dNTPs) used to synthesize DNA oligonucleotides. In some embodiments, the unincorporated nucleotides comprise nucleotide analogs. In some embodiments, the unincorporated nucleotides are modified (e.g., blocked at the 3'-OH of deoxyribose).

In some embodiments, the nucleotides are modified to prevent elongation. For example, in some embodiments, the nucleotides in the plurality of unincorporated nucleotides are 3'-OH protected nucleotides. In some embodiments, the protective group of the 3' protected nucleotides is selected from the group consisting of 3'-O-azidomethyl, 3' O allyl, 3' O methoxymethyl, 3' O nitrobenzyl, 3' O azidomethylene, and 3' O aminoalkoxyl. In embodiments in which the nucleotides are nucleotide dimers or nucleotide trimers, the 3' terminal nucleotide of the dimer or trimer may be blocked.

In some embodiments, an inhibitor of elongation is added prior to step (c) (e.g., with the polymerase or after addition of the polymerase). In some embodiments, a solution comprising $Ca^{2+}$ is added prior to step (c) to prevent further elongation. In some embodiments, the solution comprising $Ca^{2+}$ is removed in step (c) together with the plurality of templates and the excess nucleotides. In some embodiments, a solution comprising $Mg^{2+}$ is added prior to step (d) to promote incorporation of the nucleotide at the 3' terminus of the primer.

In some embodiments, the primers in the plurality of primers have the same sequence. In some embodiments, the templates in the plurality of templates have the same sequence. In embodiments in which primers have the same sequence and templates have the same sequence it is possible to synthesize a large number of oligonucleotides with the same sequence.

In some embodiments, at least two primers in the plurality of primers have different sequences. In some embodiments, at least two templates in the plurality of templates have different sequences. In embodiments in which at least two templates in the plurality of templates have different sequences, it is possible to synthesize oligonucleotides with the different sequences.

In another aspect, the disclosure features a method for synthesizing a plurality of oligonucleotides, comprising: (a) providing a plurality of immobilized primers, wherein the 5' terminus of each primer is attached to a solid support; (b) combining the plurality of immobilized primers with (i) a plurality of hairpin templates comprising between 10 and 100 nucleotides, wherein each hairpin template comprises a cleavable (e.g., phosphorothioate) linkage between the two nucleotides at the 5' terminus of each hairpin template, each hairpin template hybridizes to a primer, and the nucleotide at the 5' terminus of the hairpin template is placed adjacent to the nucleotide at the 3' terminus of the primer and (ii) a ligase. In this approach, the plurality of the immobilized primers are extended at the 3' terminus by the ligase-mediated incorporation (e.g., ligation) of the nucleotide at the 5' terminus of the hairpin template to the primer; and then (c) cleaving the cleavable linkage; (d) removing the plurality of hairpin templates; (e) repeating steps (b) to (d) until the synthesis of the oligonucleotides—is complete. In some embodiments, 4 to 100 cycles are carried out to add 4-100 nucleotides. In some embodiments, at least 10 cycles are carried out. In some embodiments, 10 to 40 cycles are carried out. In some embodiments, 10 to 25 cycles are carried out.

In some embodiments, the cleavable linkage is a phosphorothioate linkage and cleaving the phosphorothioate linkage is performed by adding a solution of $Ag^+$ or $Hg^+$. In some embodiments, each hairpin template comprises at least one non-natural nucleotide. In some embodiments, the primers in the plurality of primers have the same sequence.

In some embodiments, the hairpin templates in the plurality of hairpin templates have the same sequence. In some embodiments, at least two primers in the plurality of primers have different sequences. In some embodiments, at least two hairpin templates in the plurality of hairpin templates have different sequences.

BRIEF DESCRIPTION OF THE DRAWINGS

FIG. 7: Example demonstrating user-defined DNA synthesis with template dependent polymerases (SEQ ID NO. 4: CTCTCTCTCT).

DETAILED DESCRIPTION OF THE INVENTION

1. Introduction

Disclosed herein are compositions and methods directed to using a short template and a polymerase or ligase to synthesize an oligonucleotide. The template is designed such that only one nucleotide is added to the primer in each round of synthesis. In nature, the bulk of DNA synthesis is carried out by template dependent enzymes. Below, we describe methods and materials that enable applying these enzymes to the synthesis of user-defined DNA sequences.

Figures 1A, 1B:
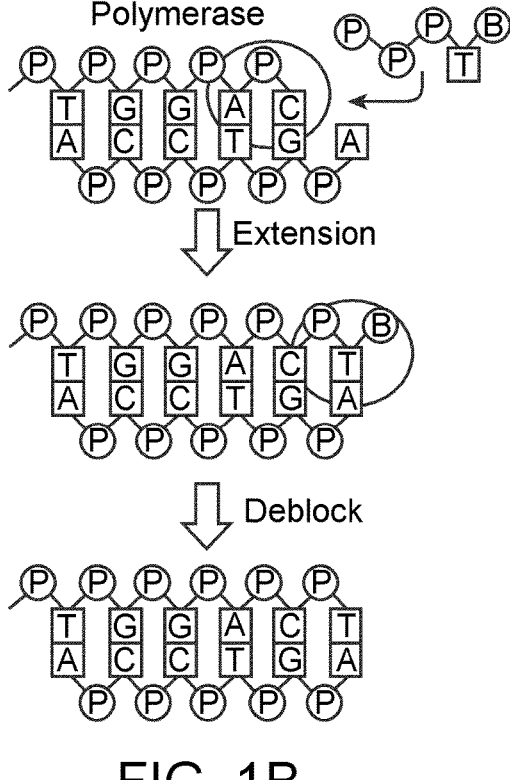
FIG. 1A: User-defined DNA synthesis with template dependent polymerases. "ATP-b" and "CTP-b" represent 3'-O-azidomethyl dATP and dCTP nucleotide reversible terminators, respectively.
FIG. 1B: User-defined DNA synthesis with template dependent polymerases. "B" represents a 3'OH blocking group.

In a first approach, we leverage the large number and efficiency of polymerases to synthesize DNA. These enzymes require a template to add a nucleotide to a strand of DNA (FIGS. 1A and 1B). We use "minimal templates," which contain the minimal sequence information and size to efficiently promote DNA elongation by a polymerase. In one approach, the minimal templates have a small number of natural nucleotides (1-6) and total length of 4-20 nucleotides. The minimal template may include non-natural nucleotides are positioned to increase duplex stability without preventing polymerase function. For example, non-natural nucleotides may be present primarily or exclusively in the 5' half of the immobilized primer. A complete set of minimal templates permits synthesis of any sequence and must contain all possible sequences of natural bases in the template. The number of templates is therefore four raised to the number of natural bases in the template, $4^1$ to $4^6$, or 4 to 4096. To reduce the complexity of the synthesis system, the templates are divided into pools, where each pool catalyzes addition of a single NTP, and the templates within the pool do not interact with other templates in the pool, so that all are available for promoting elongation.

In one approach, minimal templates are annealed to immobilized primers. The minimal templates are designed so that, when hybridized to the primers there is a one-base 5' overhang. For each immobilized primer, a nucleotide complementary to the overhang base is incorporated at the 3'end. The templates are removed and the process is repeated using a new set of templates that may be designed to anneal to the now elongated (or "growing") primers to produce a 5' overhang. Using this method, one nucleotide is added to each primer in each round, to produce oligonucleotides of a desired length and sequence(s). Templates may be designed so that all of the oligonucleotides produced in a reaction have the same sequence. Alternatively, templates may be designed to have a plurality of different defined sequences.

In some approaches, minimal templates up to 20 nucleotides in length are annealed immobilized primers to produce 5' overhang of 2 nucleotides, 3 nucleotides, or more than 3 nucleotides.

Primers may be immobilized on a support. In one approach primers are immobilized on beads. In some embodiments each bead comprises multiple copies of the same primer attached thereto. In some embodiments different beads carry different primers. In one approach primers are immobilized on a substantially planar support (e.g. an ordered array in which primers are arranged in a retilinear or other pattern). Generally, multiple copies of the same primer (i.e., primers having the same sequence) are attached at each position on an array. In some embodiments different primers are attached at different sites on an array. The number of beads in a synthesis reaction in the range of $10^3$ to $10^7$, or may be more than $10^3$, more than $10^4$, more than $10^5$, more than $10^6$, or more than $10^7$.

In some approaches reaction conditions are selected so that only one nucleotide can be incorporated in each round. In one approach blocked nucleotides complementary to the first overhang base are incorporated at the 3'end of the primer. An exemplary blocked nuclotide is a dNTP comprising a cleavable blocking group at the 3'-OH position. The blocking group prevents incorporation of additional nucleotides and prevents extension of the primer. In this approach, the templates and the blocking groups are removed, and the process is repeated using a new set of templates that may be designed to anneal to the sequence of the now-elongated (or "growing") primers to produce a 5' overhang. In some approaches, one nucleotide is added to each primer in each round, to produce oligonucleotides of a desired length and sequence(s). Templates may be designed so that all of the oligonucleotides produced in a reaction have the same sequence. Alternatively, templates may be designed to have a plurality of different defined sequences.

In one approach (which may be carried out using polymerases not compatible with 3' blocked NTPs), a chemical blocking method is used. In this method, polymerase and nucleotide (NTP or dNTP) bind to a template/primer duplex in the presence of Ca²⁺, which prevents elongation. The reagents are washed away, leaving only the polymerase and NTP bound to the primer/template duplex. Excess Mg²⁺ is then added to the reaction to promote addition of the single pre-bound NTP. The reaction stops because all NTP is consumed in a single turnover event.

In some approaches, immobilized primers are extended by 1-30 nucleotides in a process that includes multiple cycles of (i) annealing of a template to the immobilized primer to produce a partial duplex with a base 5' overhang, (ii) introducing a DNA polymerase to incorporate a modified nucleotide comprising a removable blocking group at the 3'-OH position, where the modified nucleotide binds to the overhang nucleotide based on base complementarity, (iii) removing the templates and the unincorporated nucleotides, and removing the blocking group to regenerate an extendible 3' terminus in the primer.

Figure 2:
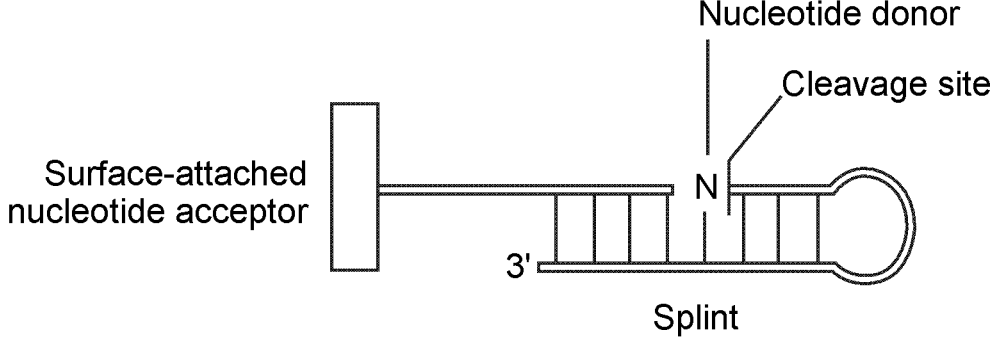
FIG. 2: Hairpin template for single base addition by a ligase.
Figure 3:
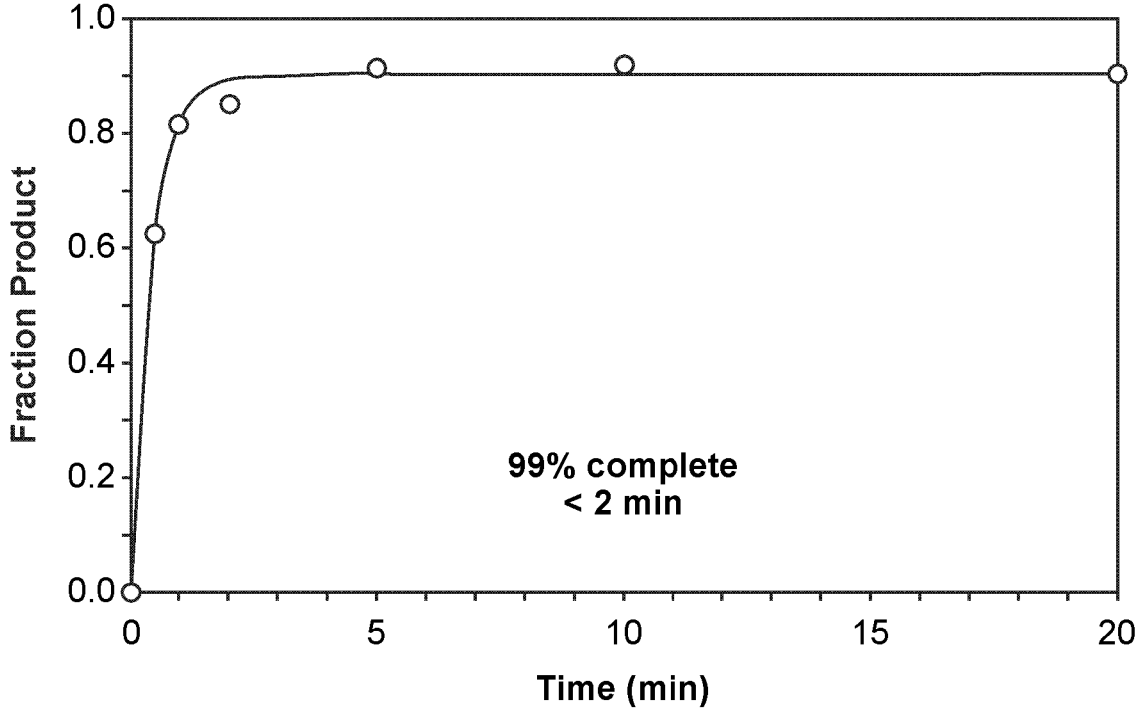
FIG. 3: Demonstration of rapid single-cycle elongation by polymerase with simple template.

In another approach, ligation reactions are used to produce oligonucleotides, e.g., oligonucleotides of defined sequence. To leverage ligases activity for DNA synthesis, a novel oligonucleotide serves as both nucleotide donor and splint (FIG. 2). This oligonucleotide consists of the nucleotide to be added, a short hairpin, and a splint complementary to the added nucleotide and a short segment of the nucleotide acceptor. 3' of the nucleotide to be added is a phosphorothioate. This bond is cleaved after the ligation reaction (e.g., with leaving only the desired nucleotide on the 3' end of ligase acceptor. Phosphorothioate may be cleaved by art-known means, such as use of a silver ion (Ag+). See, Mag et al., 1991, "Synthesis and selective cleavage of an oligodeoxynucleotide containing a bridged internucleotide 5'-phosphorothioate linkage," *Nucleic Acids Res.* 19:1437-41.

2. Definitions

As used herein, the terms "oligonucleotide," "polynucleotide," and "nucleic acid" are used interchangeably and refer to a polymeric form of nucleotides of any length, either deoxyribonucleotides or ribonucleotides or analogs thereof. An oligonucleotide can comprise modified nucleotides (e.g., non-natural nucleotides), such as methylated nucleotides and nucleotide analogs. In some embodiments, the sequence of nucleotides can be interrupted by non-nucleotide components. In some embodiments, an oligonucleotide can be further modified after polymerization, such as by conjugation with a labeling component. The term also refers to both double and single stranded molecules. Unless otherwise specified or required, any embodiment of this disclosure that is an oligonucleotide encompasses both the double stranded duplex form and each of two complementary single stranded forms known or predicted to make up the double stranded duplex form.

As used herein, the term "nucleotide" refers to, a ribonucleotide, deoxyribonucleotide, modified nucleotide (e.g., non-natural nucleotide), or any monomer component that is within an oligonucleotide or can be used to build an oligonucleotide. In some embodiments, a nucleotide comprises a nitrogenous base (also called a nucleobase), a five-carbon sugar (ribose or deoxyribose), and at least one phosphate group. A naturally occurring nucleotide may comprise the nucleobase be adenine, cytosine, guanine, thymine, or uracil. Optionally, a nucleotide has an inosine, xanthanine, hypoxanthanine, isocytosine, isoguanine, nitropyrrole (including 3-nitropyrrole), or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, dGMP, and any isomer or deaza analogs.

As used herein, the term "nucleoside" refers to a nucleobase linked to a sugar (i.e., a pentofuranosyl sugar). A nucleoside may be a naturally occurring nucleoside (i.e., adenosine, guanosine, cytidine, 5-methyluridine, or uridine) or a modified nucleoside. A modified nucleoside includes a modified nucleobase and/or a modified sugar.

As used herein, the term "primer" refers to an oligonucleotide that is to be extended using templates, nucleotides, and a polymerase. Before any extension, a primer comprises a minimum number of nucleotides, e.g., at least 4 nucleotides, in order for the first template to hybridize to the primer. In some embodiments, a primer is attached to a solid support. The term "primer" may also refer to the primer extension produced during the synthesis of the oligonucleotide. A primer is often 4 to 100 nucleotides in length, more often 5 to 50 nucleotides, more often 5 to 25 nucleotides and sometimes 5 to 15 nucleotides in length.

As used herein, the term "plurality of immobilized primers" refers to at least two or more primers that are attached to a solid support to be synthesized into oligonucleotides. The primers in the plurality of immobilized primers can have the same sequence or different sequences. In some embodments, when primers in the plurality of primers have diferent sequences, they can be extended or synthesized to produce oligonucleotides having different sequences by using templates having different sequences.

As used herein, the term "template" refers an oligonucleotide that is used by the polymerase to attach a nucleotide to the 3' terminus of the primer during the extension of the primer. A template hybridizes to the primer and has an overhang nucleotide at the 5' terminus of the template. The polymerase moves down the template in the 3' to 5' direction and adds the complement of the overhang nucleotide to the growing primer, which is extended in the 5' to 3' direction.

As used herein, the term "hairpin template" refers to a template that forms an intramolecular stem-loop structure by way of base pairing. In some embodiments, the "stem" portion of a hairpin template comprises both single-stranded regions (also called single-stranded oligonucleotides) and double-stranded regions (also called double-stranded oligonucleotides). In some embodiments, the single-stranded portion of the hairpin template hybridizes to the primer.

As used herein, the term "plurality of templates" refers to at least two or more templates used for synthesizing the oligonucleotides. In some embodiments, the plurality of templates can have the same sequence. In some embodiments, the plurality of templates have different sequences for synthesizing oligonucleotides having different sequences.

As used herein, the term "hybridize" or "hybridization" refers to the annealing of complementary nucleic acids or nucleotides through hydrogen bonding interactions that occur between complementary pairs. The hydrogen bonding interactions may be Watson-Crick hydrogen bonding or Hoogsteen or reverse Hoogsteen hydrogen bonding. Examples of complementary nucleobase pairs include, but are not limited to, adenine and thymine, cytosine and guanine, and adenine and uracil, which all pair through the formation of hydrogen bonds.

As used herein, the term "complementary" refers to the capacity for precise pairing between pairs of nucleic acids or nucleotides. For example, if a nucleotoide at a certain position of a primer is capable of hydrogen bonding with a nucleotide at the corresponding position of a template, then the nucleotide in the primer and nucleotide in the template are considered to be complementary.

As used herein, the term "overhang nucleotide" refers to a nucleotide at the 5' terminus of the template that is unpaired once the template is hybridized to the primer.

As used herein, the term "unincorporated nucleotide" refers to a nucleotide that is not attached (e.g., base-paired) to a primer or a template.

As used herein, when the term "between" is used to describe a range of values (e.g., "between 5 and 15 nucleotides") the terminal values are included (e.g., 5 nucleotides and 15 nucleotides are encompassed).

3. Methods Using Single-Stranded, Linear Templates

The disclosure provides methods for synthesizing oligonucleotides that use short, single-stranded, linear templates. The methods comprise: (a) providing a plurality of immobilized primers, wherein the 5' terminus of each primer is attached to a solid support; (b) combining the plurality of immobilized primers and (i) a plurality of templates comprising between 2 and 100 nucleotides, wherein each template hybridizes to a primer with one overhang nucleotide at the 5' terminus of the template; (ii) a plurality of unincorporated nucleotides; and (iii) a polymerase; wherein the plurality of the immobilized primers are extended at the 3' terminus by the polymerase-mediated incorporation of one unincorporated nucleotide, wherein the incorporated nucleotide is complementary to the overhang nucleotide of the template hybridized to the primer; and then (c) removing the hybridized templates and excess unincorporated nucleotides; and (d) repeating steps (b) and (c) one or more times until the synthesis of the oligonucleotide is complete.

In one approach the methods feature short, single-stranded, linear templates with a total length of 4-20 nucleotides. In other approaches the short, single-stranded, linear templates have between 2 and 100 (e.g., between 2 and 90, between 2 and 80, between 2 and 70, between 2 and 60, between 2 and 50, between 2 and 40, between 2 and 30, between 2 and 20, between 2 and 10, between 2 and 9, between 2 and 8, between 2 and 7, between 2 and 6, between 2 and 5, between 2 and 4, between 4 and 90, between 6 and 90, between 8 and 90, between 10 and 90, between 20 and 90, between 30 and 90, between 40 and 90, between 50 and 90, between 60 and 90, between 70 and 90, or between 80 and 90) nucleotides. As noted, in each round of synthesis, templates hybridize to primers (including primers elongated in previous rounds) based on nucleobase complementarity. In some embodiments, in one or more rounds of nucleotide incorporation, the templates in the plurality of templates have the same sequence. When the templates in the plurality of templates have the same sequence, the primers to which the templates anneal will share the same sequence. Thus, the oligonucleotides synthesized also share the same sequence. In other embodiments, for reach round of nucleotide incorporation, templates in the plurality of templates do not all have the same sequence, i.e., the templates have different sequences. When the templates in the plurality of templates have different sequences, each template anneals to a primer having the complementary sequence. In this case, the oligonucleotides synthesized generally have different sequences.

In some embodiments, the primer and/or template used can contain one or more non-natural nucleotides. In particular embodiments, the template can contain one or more non-natural nucleotides. The presence of non-natural nucleotides in a primer or template can promote the stability of the primer or template. In some embodiments, the presence of non-natural nucleotides in a template can prevent non-specific annealing among templates. Examples of non-natural nucleotides are described in detail hereinbelow.

Figure 4:
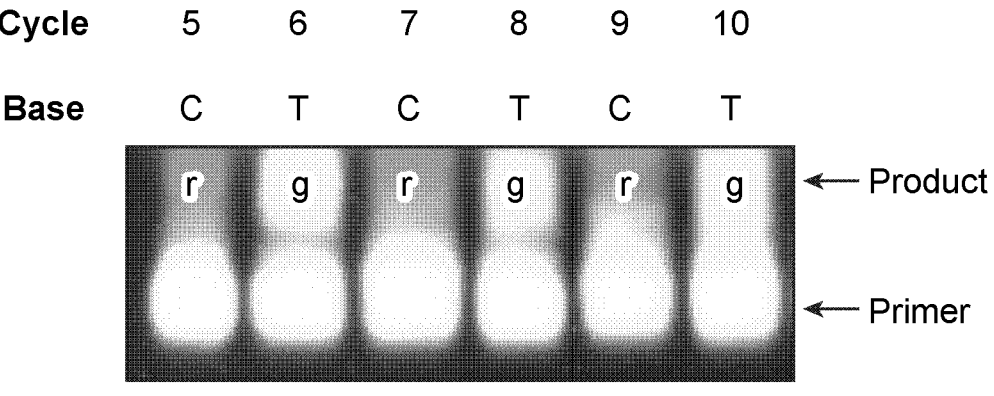
FIG. 4: Demonstration of 10 cycle synthesis with polymerase using simplified templates. "r" and "g" represent differently labeled extension products.
Figure 5:
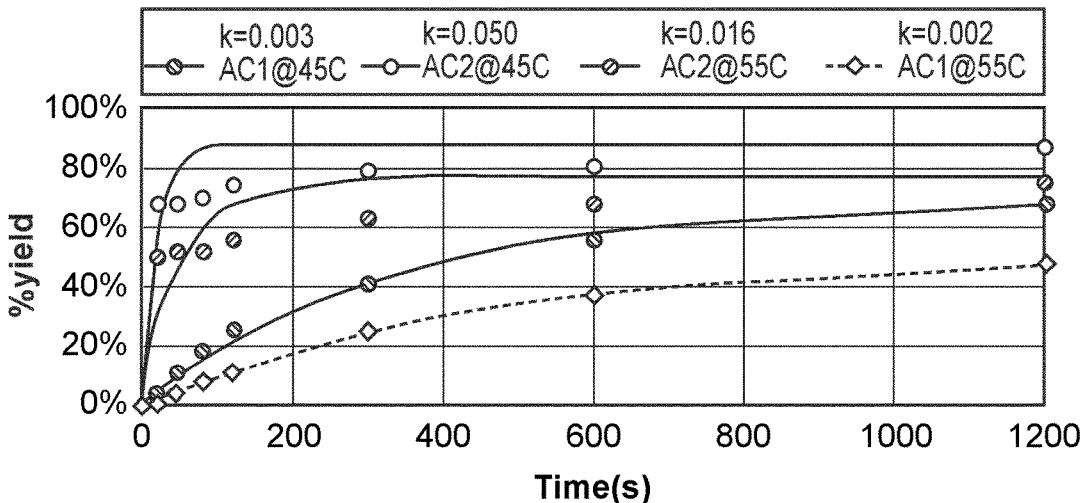
FIG. 5: Example of effect of primer sequence on elongation efficiency.
Figure 6:
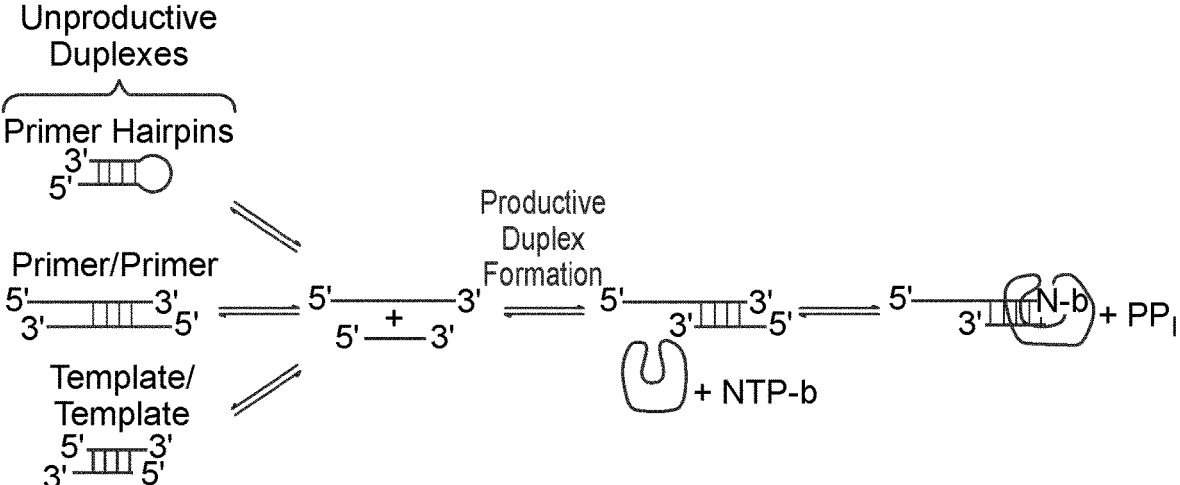
FIG. 6: Templates are engineered to maximize productive duplex formation relative to other formation of other duplexes.

To extend the primer, the polymerase moves down the template in the 3' to 5' direction and incorporates a nucleotide into the growing primer (i.e., the process of elongation), where the nucleotide that incoporated is the complement of the overhang nucleotide of the annealed template, and the growing primer is extended in the 5' to 3' direction. In some embodiments, the nucleotide used by the polymerase can be a 3' protected (or blocked) nucleotide. For example, the 3' protective group can be selected from the group consisting of 3'-O-azidomethyl, 3'-O-allyl, 3'-O-methoxymethyl, 3'-O-nitrobenzyl, 3'-O-azidomethylene, and 3'-O-aminoalkoxyl. Typically such a modified nucleotide (dNTP) is referred to as a "reversible terminator." Reversible terminators are well known in the art (see, e.g., WO 2018/129214, e.g., at FIG. 4). Methods for chemical removal of blocking groups (deprotection) are known in the art. In one embodiment 3'-O azidomethyl groups are removed using a phosphine ligand such as tris(hydroxylpropyl)phosphine (THPP). As another example, blocking groups containing an alkynyl group may be removed by a Pd(II) complex in the presence of THPP.

In some embodiments of the methods, a solution that inhibits elongation is added prior to the "step (c)" removing the hybridized templates and excess unincorporated nucleotides. In particular embodiments, a solution that inhibits elongation contains $Ca^{2+}$. Once the nucleotide complementary to the overhang nucleotide at the 5' terminus of the template is positioned at the 3' terminus of the growning primer, a solution comprising $Ca^{2+}$ can be added. The solution comprising the inhibitor (e.g., $Ca^{2+}$) can be removed, together with the plurality of templates and the excess nucleotides. In this manner, elongation is inhibited until the excess unincorporated nucleotides and the plurality of templates are removed from the synthetic reaction.

A solution that promotes incorporation of the nucleotide can also be added after step (c) or before step (c). A solution that promotes incorporation of the nucleotide can contain $Mg^{2+}$.

3.1 Polymerase

In methods that use short, single-stranded, linear templates to synthesize oligonucleotides, nucleic acid polymerase enzymes are able to catalyze the production of new oligonucleotides from an existing primer. There are many different types of polymerases including DNA polymerases, RNA polymerases and reverse transcriptases that are suitable for use in the invention. RNA polymerases catalyze the polymerization of an RNA strand from a DNA template in the process of transcription. It then produces an RNA chain which is complementary to the DNA strand used as a template. The process of adding nucleotides to the RNA strand is an example of the process of elongation. In some cases an RNA polymerases can initiate transcription at specific DNA sequences known as promoters. For example and not limitation, exemplary DNA polymerases include DNA polymerase I, T4 DNA polymerase, T7 DNA polymerase, Taq polymerase, Thermococcus onnurineus NA1 (TNA1) polymerase, Pfu DNA polymerase, Thermococcus peptonophilus (Tpe) DNA polymerase, Avian Myeloblasto-sis Virus (AMV) reverse transcriptase, Moloney Murine Leukemia Virus (M-MLV) reverse transcriptase, and KOD DNA polymerase. Descriptions of polymerases can be found in, e.g., Sambrook and Russell, Molecular Cloning, A Labo-ratory Manual, Cold Spring Harbor Press, 4th ed. (2012).

During the process of replication, the overhang nucleotide sequence of a template strand is copied by complementary base-pairing into a complementary nucleic acid sequence that is added to the 3' terminus of the growing primer. The appropriate incoming single nucleotides are thereby aligned for their enzyme-catalyzed polymerization into a growing primer.

Enzymes having DNA polymerase activity catalyze the formation of a bond between the 3' hydroxyl group at the growing end of a primer sequence and the 5' phosphate group of a nucleotide triphosphate. In some embodiments, the plurality of nucleotides provided can contain modified or non-natural nucleotides and the polymerase can incorporate the altered versions of these nucleotides.

4. Methods Using Hairpin Templates

The disclosure provides methods for synthesizing oligo-nucleotides that use hairpin templates. The methods com-prise: (a) providing a plurality of immobilized primers, wherein the 5' terminus of each primer is attached to a solid support; (b) combining the plurality of immobilized primers with a plurality of hairpin templates and a ligase. The plurality of hairpin templates each may comprise between 10 and 100 nucleotides, wherein each hairpin template comprises a cleavable linkage between the two nucleotides at the 5' terminus of the hairpin template. In some embodi-ments the cleavable linkage is a phosphorothioate linkage. Each hairpin template hybridizes to an immobilized primer, and the nucleotide at the 5' terminus of the hairpin template is placed or positioned so that it is adjacent to the nucleotide at the 3' terminus of the primer. The plurality of the immobilized primers are extended at the 3' terminus by the ligase-mediated incorporation of the nucleotide at the 5' terminus of the hairpin template (i.e., resulting from the linkage of the 5' nucleotide of the template and the 3' nucleotide of the primer). The cleavable linkage (e.g., phos-phorothioate linkage) is cleaved (step (c)) and the plurality of hairpin templates are removed (step (d)). Steps (b) to (d) are repeated for multiple cycles or rounds until the synthesis of the oligonucleotide is complete. In some embodiments, 4 to 100 cycles are carried out to add 4-100 nucleotides. In some embodiments, at least 10 cycles are carried out. In some embodiments, 10 to 40 cycles are carried out. In some embodiments, 10 to 25 cycles are carried out.

The hairpin templates may have between 10 and 100 (e.g., between 20 and 100, between 30 and 100, between 40 and 100, between 50 and 100, between 60 and 100, between 70 and 100, between 80 and 100, between 90 and 100, between 10 and 90, between 20 and 90, between 30 and 90, between 40 and 90, between 50 and 90, between 60 and 90, between 70 and 90, or between 80 and 90) nucleotides. As described in FIG. 2, the hairpin template contains an intramolecular stem-loop structure by way of base pairing. The "stem" portion of the hairpin template can contain both single-stranded oligonucleotides (or regions) and double-stranded oligonucleotides (or regions). In some embodiments, the single-stranded portion of the stem in the hairpin template hybridizes to the corresponding complementary portion of the primer. In some embodiments, for reach round of nucleo-tide incorporation, the templates in the plurality of templates have the same sequence. When the templates in the plurality of templates have the same sequence, the templates anneal to the primers having the same sequence. Thus, the oligo-nucleotides synthesized also share the same sequence. In other embodiments, for reach round of nucleotide incorpo-ration, the templates in the plurality of templates have different sequences. When the templates in the plurality of templates have different sequences, each template anneals to a primer having the complementary sequence. Thus, the oligonucleotides synthesized have different sequences.

In some embodiments, the primer and/or hairpin template used can contain one or more non-natural nucleotides. In particular embodiments, the hairpin template can contain one or more non-natural nucleotides. The presence of non-natural nucleotides in a primer or hairpin template can promote the stability of the primer or hairpin template. In some embodiments, the non-natural nucleotides are present in the stem portion of a hairpin template. In some embodi-ments, the presence of non-natural nucleotides in a hairpin template can prevent non-specific annealing among tem-plates. Examples of non-natural nucleotides are described herein above.

In methods for synthesizing oligonucleotides that use hairpin templates described herein, the linkage between the last two nucleotides at the 5' terminus of the hairpin template may be a phosphorothioate linkage. Once the last nucleotide at the 5' terminus of the hairpin template is ligated to the 3' terminus of the growing primer by the ligase, the phospho-rothioate linkage can be cleaved. In some embodiments, a solution containing Ag+ can be added to cleave the phos-phorothioate linkage in step (c) of the method. In other embodiments, a solution containing Hg+ can be added to cleave the phosphorothioate linkage in step (c) of the method.

4.1 Ligase

In methods for synthesizing oligonucleotides that use hairpin templates described herein, a ligase facilitates the joining of a nucleotide (e.g., the last nucleotide at the 5' terminus of the hairpin template) to the 3' terminus of the growing primer by catalyzing the formation of a phosphodi-ester bond. A ligase used in methods described herein can also join a non-natural nucleotide to the 3' terminus of the growing primer. For example and not limitation, exemplary DNA ligases include T3 DNA ligase, T4 DNA ligase, T5 DNA ligase, T7 DNA ligase, Taq DNA ligase, vaccinia virus DNA ligase, E. coli DNA ligase, mammalian DNA ligase I, mammalian DNA ligase II, mammalian DNA ligase III, Tth DNA ligase, and Tfl DNA ligase. Descriptions of ligases can be found in, e.g., Sambrook and Russell, Molecular Cloning, A Laboratory Manual, Cold Spring Harbor Press, 4th ed. (2012), and suitable DNA ligases include those described in, for example, U.S. Pat. Nos. 6,194,637; 6,444,429; 6,455, 274; 6,576,453; and 6,635,425.

5. Examples

A 27-mer primer with biotin at the 5' end was obtained from IDT (Coralville, Iowa). The primer sequence was 5'-biotin-TTT TTN CCT AGG AGT GAT GCA CAC-3' (biotin linked to 5' end of SEQ ID NO:1). 'N' stands for inosine, and inosine serves a specific site to cleave the product DNA from the beads after synthesis was complete. The biotin attaches the DNA to magnetic streptavidin beads. This primer was further referred to as 'Biotin-AC' primer.

Bind and wash (B&W) buffer was prepared (10 mM Tris-HCl pH7.5, 1 mM EDTA, 2 M NaCl) at 2× and 1× concentration. 30 μL of Dynabeads MyOne Streptavidin C1 beads (Invitrogen, Thermo Fisher Scientific) were acquired and washed with 400 μL 1× B&W buffer to remove the storage buffer. Washing the beads consists of adding buffer, pulling down the beads with a magnet, and removing the buffer. The beads then were washed 3 more times with 120 μL 1× B&W buffer. 30 μl of 20 μM Biotin-AC primer was added to the washed beads along with 30 μL of 20 uM free biotin and 60 μL 2× B&W buffer. After mixing well, the mixture was rotated at room temperature for 10 minutes. The beads were then pulled down with magnet, washed two times with 30 μL 1× B&W buffer, and washed two times with 30 μL reaction buffer (0.05 M Trizma Base, 0.05 M NaCl, 0.001 M EDTA, 3.1 mM MgSO$_4$, 0.05% Tween-20, 0.0625 M (NH$_4^+$)$_2$SO$_4$, 5% DMSO). 10 μL of beads suspension were removed after the reaction buffer was added for the second wash as the "Primer" sample, which was later analyzed by HPLC. The remaining beads with were used for base extension.

Two unique 6-mer templates from IDT were used for extension of the primer. TG1 (5'-TGTGTG-3' (SEQ ID NO:2)) was used for the first base (dA) addition and TG2 (5'-GTGTGT-3' (SEQ ID NO:3)) was used for the second base (dC) addition. Each template was dissolved to a concentration of 5 mM. Reaction solution for the first base addition was prepared by mixing 4 μL TG1, 2 μL 100 mM MgSO$_4$, 2 μL 3'-azidomethyl-dA, 5 μl polymerase (BGI Research), 7 μL ICB buffer. The primer-incorporated beads were resuspended in the reaction mix and incubated at 45° C. for 30 minutes. After the reaction, the beads were washed with 30 μL high salt wash buffer (50 mM Tris, 500 mM NaCl, 0.1 mM EDTA, 0.05% Tween20, pH8.0) and then 30

μL low salt wash buffer (50 mM Tris, 150 mM NaCl, 0.05% Tween20, pH8.0). The 3'-azidomethyl protecting group was then removed by incubating beads in 20 μl regeneration reagent (0.013M THPP) for 2 minutes at 45° C. The beads were then washed with 20 μL high salt wash buffer and 10 μL of the beads suspension was removed for analysis as the "Primer+1" sample. The remaining beads were washed once more with ICB buffer and ready for the next addition.

The second base addition reaction solution was prepared by mixing 2 μL TG2, 1 μL 100 mM MgSO$_4$, 1 μL 3'-azidomethyl-dC, 2.5 μl polymerase, 3.5 μL reaction buffer. The beads attached to primer-AC+A were suspended in this reaction solution and incubated at 45° C. for 30 minutes. After the reaction, beads were pulled down, and again washed with 20 μL high salt wash buffer and 20 μL low salt wash buffer. Then 3'azidomethyl was removed by incubating beads in 10 μL regeneration reagent for 2 minutes and 45° C. 10 μL high salt wash buffer was then used to resuspend the beads and this will be taken as "Primer+2" sample.

The three samples, "Primer", "Primer+1", and "Primer+2", were washed twice with nuclease free water. Then solution for cleaving the product DNA from the beads was prepared by mixing 1 μL Endonuclease V (New England Biolab), 3.5 μL 10× Buffer 4.0 (New England Biolab), and 30.5 μL nuclease free water. 7 μL of this solution was added to each sample of beads. The suspension was incubated at 37° C. for 1 hour. The beads were then pulled down and supernatant was collected to be analyzed by HPLC.

The cleaved samples, "Primer", "Primer+1", and "Primer+2", were then transferred to HPLC vials and run on reverse-phase HPLC using an ion-pairing agent (triethylamine acetate) and a gradient of acetonitrile. Clear single peaks were observed with different retention time, so we conclude that two nucleotides were added to the surface attached primer with high efficiency in two reaction cycles.

---

What is claimed is:

1. A method for synthesizing an oligonucleotide, comprising:

(a) providing a plurality of immobilized primers, wherein the 5' terminus of each primer is attached to a solid support;

(b) combining the plurality of immobilized primers and (i) a plurality of templates comprising between 2 and 100 nucleotides, wherein each template hybridizes to a primer generating a single overhang nucleotide at the 5' terminus of the template;

(ii) a plurality of unincorporated nucleotides; and (iii) a polymerase;

wherein the plurality of the immobilized primers are extended at the 3' terminus by the polymerase-mediated incorporation of a single unincorporated nucleotide, wherein the single incorporated nucleotide is complementary to the single overhang nucleotide of the template hybridized to the primer; and then (c) removing the hybridized templates and excess unincorporated nucleotides; and (d) repeating steps (b) and (c) multiple times until the synthesis of the oligonucleotide is complete.

2. The method of claim 1, wherein the nucleotides in the plurality of nucleotides are 3' protected nucleotides.

3. The method of claim 2, wherein the protective group of the 3' protected nucleotides is selected from the group consisting of 3'-O-azidomethyl, 3'-O-allyl, 3'-O-methoxymethyl, 3'-O-nitrobenzyl, 3'-O-azidomethylene, and 3'-O-aminoalkoxyl.

4. The method of claim 1, wherein a solution comprising $Ca^{2+}$ is added prior to step (c) to prevent further elongation.

5. The method of claim 4, wherein the solution comprising $Ca^{2+}$ is removed in step (c) together with the plurality of templates and the excess nucleotides.

6. The method of claim 5, wherein a solution comprising $Mg^{2+}$ is added prior to step (d) to promote incorporation of the nucleotide to the 3' terminus of the primer.

7. The method of claim 1, wherein the templates in the plurality of templates comprise between 5 and 50 nucleotides.

8. The method of claim 1, wherein the templates in the plurality of templates comprise between 5 and 20 nucleotides.

9. The method of claim 1, wherein the primers in the plurality of primers have the same sequence.

10. The method of claim 9, wherein the templates in the plurality of templates have the same sequence.

11. The method of claim 1, wherein at least two primers in the plurality of primers have different sequences.

12. The method of claim 11, wherein at least two templates in the plurality of templates have different sequences.

13. A method for synthesizing an oligonucleotide, comprising:

(a) providing a plurality of immobilized primers, wherein the 5' terminus of each primer is attached to a solid support;

(b) combining the plurality of immobilized primers and (i) a plurality of hairpin templates comprising between 10 and 100 nucleotides, wherein each hairpin template comprises a phosphorothioate linkage between the two nucleotides at the 5' terminus of each hairpin template, each hairpin template hybridizes to a primer, and the nucleotide at the 5' terminus of the hairpin template is placed adjacent to the nucleotide at the 3' terminus of the primer;

(ii) a ligase;

wherein the plurality of the immobilized primers are extended at the 3' terminus by the ligase-mediated incorporation of the nucleotide at the 5' terminus of the hairpin template; and then (c) cleaving the phosphorothioate linkage;

(d) removing the plurality of hairpin templates;

(e) repeating steps (b) to (d) until the synthesis of the oligonucleotide is complete.

14. The method of claim 13, wherein cleaving the phosphorothioate linkage is performed by adding a solution of $Ag^+$ or $Hg^+$.

15. The method of claim 13, wherein each hairpin template comprises at least one non-natural nucleotides.

16. The method of claim 13, wherein the primers in the plurality of primers have the same sequence.

17. The method of claim 16, wherein the hairpin templates in the plurality of hairpin templates have the same sequence.

18. The method of claim 13, wherein at least two primers in the plurality of primers have different sequences.

19. The method of claim 18, wherein at least two hairpin templates in the plurality of hairpin templates have different sequences.

* * * * *

SEQUENCE LISTING

```
<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Primer sequence
<220> FEATURE:
<221> NAME/KEY: misc_feature
<222> LOCATION: (6)..(6)
<223> OTHER INFORMATION: N is Inosine

<400> SEQUENCE: 1
tttttnccta ggagtgatgc acac                                          24

<210> SEQ ID NO 2

<400> SEQUENCE: 2

000

<210> SEQ ID NO 3

<400> SEQUENCE: 3

000

<210> SEQ ID NO 4
<211> LENGTH: 10
```

-continued

<212> TYPE: DNA
<213> ORGANISM: Artificial Sequence
<220> FEATURE:
<223> OTHER INFORMATION: The sequence is artificially synthesized

<400> SEQUENCE: 4
ctctctctct                                                          10